(12) United States Patent
Glaser et al.

(10) Patent No.: US 9,261,442 B2
(45) Date of Patent: Feb. 16, 2016

(54) ACOUSTIC PRESSURE WAVE/SHOCK WAVE MEDIATED PROCESSING OF BIOLOGICAL TISSUE, AND SYSTEMS, APPARATUSES, AND METHODS THEREFOR

(71) Applicant: Microbrightfield, Inc., Williston, VT (US)

(72) Inventors: Jacob R. Glaser, Williston, VT (US); Christoph Schmitz, Wuerselen (DE); Andreas Menne, Taegerwilen (CH)

(73) Assignee: Microbrightfield, Inc., Williston, VT (US)

( * ) Notice: Subject to any disclaimer, the term of this patent is extended or adjusted under 35 U.S.C. 154(b) by 0 days.

(21) Appl. No.: 14/361,567

(22) PCT Filed: Nov. 30, 2012

(86) PCT No.: PCT/US2012/067183
§ 371 (c)(1),
(2) Date: May 29, 2014

(87) PCT Pub. No.: WO2013/082352
PCT Pub. Date: Jun. 6, 2013

(65) Prior Publication Data
US 2014/0335511 A1    Nov. 13, 2014

Related U.S. Application Data

(60) Provisional application No. 61/565,552, filed on Dec. 1, 2011.

(51) Int. Cl.
G01N 1/30    (2006.01)
G01N 1/31    (2006.01)
G01N 1/28    (2006.01)
G01N 1/44    (2006.01)

(52) U.S. Cl.
CPC .................. *G01N 1/31* (2013.01); *G01N 1/286* (2013.01); *G01N 1/44* (2013.01)

(58) Field of Classification Search
None
See application file for complete search history.

(56) References Cited

U.S. PATENT DOCUMENTS

| | | | |
|---|---|---|---|
| 6,291,180 | B1 | 9/2001 | Chu |
| 6,413,230 | B1 | 7/2002 | Haupt et al. |
| 2004/0142463 | A1 | 7/2004 | Walker et al. |
| 2005/0209586 | A1 | 9/2005 | Menne et al. |
| 2006/0153736 | A1 | 7/2006 | Kalra et al. |
| 2009/0155907 | A1 | 6/2009 | Winther et al. |
| 2010/0068690 | A1 | 3/2010 | Liotta et al. |

FOREIGN PATENT DOCUMENTS

WO    2010/010355 A2    1/2010

OTHER PUBLICATIONS

PCT International Search Report dated Apr. 3, 2013, for related PCT/US2012/067183 filed Nov. 30, 2012, entitled "Acoustic pressure wave/shock wave mediated processing of biological tissue, and systems, apparatuses, and methods therefor," Glaser et al.

*Primary Examiner* — Jim Ketter
(74) *Attorney, Agent, or Firm* — Downs Rachlin Martin PLLC

(57) ABSTRACT

Methods for preparing a biological tissue specimen for examination, such as microscopic examination, that involves applying acoustic pressure wave/shock wave (APW/SW) energy to the tissue specimen. The APW/SW energy can be applied to the tissue specimen to augment any one or more steps of processing the tissue specimen. In one example, the APW/SW energy is applied to enhance histotechnological processing of the tissue specimen. Apparatuses and systems that include APW/SW generators and that are specifically configured for processing biological tissue specimens are also disclosed.

16 Claims, 4 Drawing Sheets

ACOUSTIC PRESSURE WAVE/SHOCK WAVE MEDIATED PROCESSING OF BIOLOGICAL TISSUE, AND SYSTEMS, APPARATUSES, AND METHODS THEREFOR

RELATED APPLICATION DATA

This application claims the benefit of priority of U.S. Provisional Patent Application Ser. No. 61/565,552, filed on Dec. 1, 2011, and titled "ACOUSTIC PRESSURE WAVE/ SHOCK WAVE MEDIATED PROCESSING OF BIOLOGICAL TISSUE, AND SYSTEMS, APPARATUSES, AND METHODS THEREFOR," which is incorporated by reference herein in its entirety.

FIELD OF THE INVENTION

The present invention generally relates to the field of histology. In particular, the present invention is directed to acoustic pressure wave/shock wave mediated processing of biological tissue, and systems, apparatuses, and methods therefor.

BACKGROUND

A multitude of methods is known in the art for processing biological tissue for microscopic examination, often collectively referred to as "histotechnology." Such methods are in worldwide use nowadays and have become of paramount importance for countless applications of microscopy in basic science, clinical science, clinical routine, toxicology, and pharmaceutical and biotechnological research and development. For instance, staining tissue specimens/sections with dyes and/or processing them with immunohistochemistry (IHC) is used in virtually every clinical pathology laboratory for the diagnosis of abnormal cells such as those found in cancerous tumors. IHC is also used in almost every biomedical research laboratory to understand the distribution and localization of biomarkers and differentially expressed proteins in different parts of a biological tissue. For instance, specific molecular markers are characteristic of particular cell types, such as CD8 for cytotoxic T cells and NeuN for neurons (to mention only a few). Other molecular markers are characteristic of particular cellular events, such as proliferation (addressing the cell cycle) or cell death (apoptosis). RNA in situ hybridization (ISH) can be used to localize and measure messenger RNAs (mRNAs) and other DNA transcripts within tissue sections or whole mounts of tissue specimens. DNA ISH can be used to determine the structure of chromosomes. A common application of fluorescent DNA ISH (FISH) is the assessment of chromosomal integrity in medical diagnostics. As those skilled in the art will appreciate, the present description of applications of the methods for processing biological tissue for microscopic examination is intended in an illustrative rather than in a limiting sense.

Despite their worldwide use in countless applications of microscopic analysis, none of the conventional methods known in the art for processing biological tissue for microscopic examination can be considered perfect. For instance, washing tissue specimens/sections can result in incomplete and/or uneven cleaning; fixing tissue specimens/sections can result in incomplete and/or uneven fixation and/or even or uneven over-fixation; dehydrating tissue specimens/sections can result in incomplete and/or uneven dehydration and/or even or uneven over-dehydration; hydrating tissue specimens/sections can result in incomplete and/or uneven hydration and/or even or uneven over-hydration; clearing tissue specimens/sections can result in incomplete and/or uneven clearing and/or even or uneven over-clearing; embedding tissue specimens/sections into an embedding medium can result in incomplete and/or uneven embedding and/or even or uneven over-embedding; mounting tissue specimens/sections with a mounting medium can result in incomplete and/or uneven mounting and/or even or uneven overmounting; cryoprotecting tissue specimens/sections can result in incomplete and/or uneven cryoprotection and/or even or uneven over-cryoprotection; freezing tissue specimens/sections can result in incomplete and/or uneven freezing and/or even or uneven over-freezing; thawing tissue specimens/sections can result in incomplete and/or uneven thawing and/or even or uneven over-heating; removing embedding medium from tissue specimens/sections can result in incomplete and/or uneven removing of the embedding medium and/or even or uneven removing of more than just the embedding medium; staining tissue specimens/sections can result in incomplete and/or uneven staining and/or even or uneven over-staining; processing tissue specimens/sections with histochemistry can result in incomplete and/or uneven histochemical processing and/or even or uneven over-processing; processing tissue specimens/sections with immunohistochemistry (IHC) and/or fluorescence immunohistochemistry/immunofluorescence (IF) can result in incomplete and/or uneven detection of antigens and/or even or uneven cross-reactions with other antigens to which the applied antibodies and/or antibody mimetics do not bind specifically, as well as in incomplete and/or uneven counterstaining and/or even or uneven over-counterstaining in IHC and IF, and processing tissue specimens/sections with in situ hybridization (ISH) and/or fluorescence in situ hybridization (FISH) can result in incomplete and/or uneven hybridization of labeled complementary DNA or RNA strands to specific DNA or RNA sequences and/or even or uneven cross-reactions with other DNA or RNA sequences to which the applied labeled complementary DNA or RNA strands do not hybridize specifically, as well as in incomplete and/or uneven counterstaining and/or even or uneven over-counterstaining in ISH and FISH.

Moreover, the various sub-steps of washing, fixing, dehydrating, hydrating, clearing, embedding, mounting, cryoprotecting, freezing, thawing, and/or staining tissue specimens/sections, removing embedding medium from tissue specimens/sections, and/or processing tissue specimens/sections with histochemistry, IHC, IF, ISH and/or FISH can last between a few seconds and several months and are, thus, very time-consuming as well as tedious and cumbersome. Besides this, the various sub-steps require the use of various chemicals, media, antibodies, antibody mimetics, and labeled DNA or RNA strands, many of which cost between a few dollars and thousands of dollars and, thus, are very expensive. Additionally, many of the chemicals used in the various sub-steps are regarded as being toxic and, thus, pose a potential threat not only to the health and life of those performing the methods for processing biological tissue for microscopic examination, but also to the environment. As those skilled in the art will appreciate, the present description of shortcomings, time requirements, costs, and hazard potential of the conventional methods for processing biological tissue for microscopic examination is intended in an illustrative rather than in a limiting sense.

Several methods are known that aim at improving individual histotechnological procedures for these various sub-steps for microscopic examination. For instance, U.S. Pat. No. 5,244,787 to Key et al., issued on Sep. 14, 1993, teaches a method of immunologically staining a formalin-fixed tissue specimen that comprises subjecting a formalin-fixed tissue specimen to microwave energy while the tissue specimen is submersed in water for a time sufficient to increase immunostaining efficiency (known in the art as "antigen retrieval"), removing the tissue specimen from the water and cooling, and contacting the tissue specimen with an immunological staining reagent. U.S. Pat. No. 5,578,452 to Shi et al., issued on Nov. 26, 1996, teaches a method for restoring immunoreactivity of a tissue specimen fixed with an aldehyde fixing agent and embedded in an embedding medium by contacting the tissue specimen with a solvent for the embedding medium and an aldehyde releasing reagent, which reagent releases aldehyde from the tissue by reacting the aldehyde in a substantially irreversible manner to form a non-aldehyde derivative, and removing or neutralizing excess aldehyde releasing reagent from the tissue specimen. U.S. Pat. No. 7,067,325 to Christensen et al., issued on Jun. 27, 2006, teaches an automated method of removing paraffin based embedding medium from tissue specimens without the dependence on organic solvents by applying a deparaffinizing and antigen retrieval reagent that includes a detergent to the tissue specimen, and applying heat to the tissue specimen to melt the paraffin based embedding medium, to mention only a few.

However, none of these methods have addressed known histotechnology procedures, such as the sub-steps listed above, as a whole, and the application of certain chemicals and particularly the application of heat during tissue processing can challenge tissue integrity substantially and, thus, clarity and detectability of microscopic details when examining tissue specimens/sections under a microscope.

Recently, a number of ultrasound-based methods were described that aim at improving one or more of the known histotechnology procedures. The term "ultrasound" usually refers in the art to cyclic sound pressure/acoustic waves having a frequency greater than the upper limit of human hearing, i.e., typically above 20 KHz. For example, U.S. Pat. No. 3,961,097 to Gravlee, issued on Jun. 1, 1976, teaches a method for preparing tissue specimens for microscopic examination, including the steps of fixing, dehydrating, clearing, and impregnating tissue specimens with paraffin, and applying low frequency ultrasound (50 KHz) to tissue specimens in each of these processing steps in order to reduce the total preparation time. Likewise, U.S. Pat. No. 5,089,288 to Berger, issued on Feb. 18, 1992, teaches a method for impregnating tissue specimens with paraffin, including the steps of fixing, dehydrating, and embedding tissue specimens in paraffin, with exposure of the tissue specimen to low frequency ultrasound (35-50 KHz) during paraffin embedding in a closed, evacuated working chamber. However, these methods suffer from potential tissue damage due to the low frequency of the applied ultrasound, as demonstrated in many studies reviewed in U.S. Pat. No. 7,090,974 to Chu, issued on Aug. 15, 2006 ("the '974 patent").

The '974 patent is part of a series of related U.S. patents issued to Chu, all entitled "Ultrasound-mediated high-speed biological reaction and tissue processing" (U.S. Pat. No. 6,291,180 issued on Sep. 18, 2001; U.S. Pat. No. 7,090,974 issued on Aug. 15, 2006; U.S. Pat. No. 7,262,022 issued on Aug. 28, 2007; U.S. Pat. No. 7,687,255 issued on Mar. 30, 2010; and U.S. Pat. No. 7,767,434 issued on Aug. 3, 2010), and teaches a method that is directed to using high intensity, high frequency, nondestructive, wide-band ultrasound for tissue fixation and processing in conjunction with well-known techniques to decrease the time required to perform the techniques, including immunological reactions, hybridizations, tissue fixation and processing. According to the Chu method, the tissue specimens/sections must receive at least 10 W/cm$^2$ of fairly even distributed ultrasound using a single high frequency or using wide-band frequencies within the range of 0.1-50 MHz.

However, the Chu method suffers from several drawbacks. First, it requires very special and presumably very expensive technology to produce ultrasound transducers that are capable of delivering such high-frequency, high-intensity ultrasound. Second, the '974 patent discloses that the high-frequency, high-intensity ultrasound exposes tissue specimens/sections to heat and, thus, can challenge tissue integrity substantially and, thus, clarity and detectability of microscopic details when examining tissue specimens/sections under a microscope. Third, the Chu method does not disclose any improvement over prior art with respect to reducing the amount of media and/or chemicals necessary to carry out one or more or all steps of the procedures of histotechnology (except of dyes, antibodies and/or antibody mimetics, and/or labeled DNA and/or RNA strands), with many of these media and chemicals regarded being toxic. Fourth, the method does not disclose any improvement over prior art with respect to increasing the penetration depth of dyes, antibodies and/or antibody mimetics, and/or labeled DNA and/or RNA strands into the thickness of a tissue specimen/section.

SUMMARY OF THE DISCLOSURE

In one implementation, the present disclosure is directed to a method of processing biological tissue for microscopic examination. The method includes obtaining a tissue specimen from the biological tissue; processing the tissue specimen so as to prepare a processed specimen for examination; and subjecting the tissue specimen to at least one acoustic pressure wave/shock wave (APW/SW) so as to provide an improvement in 1) the processing, 2) a result of at least one procedures used in the processing, and/or 3) an aspect of the processed specimen, relative to the method being performed without the subjecting the tissue specimen to the at least one APW/SW.

In another implementation, the present disclosure is directed to an apparatus that includes a tissue-specimen receiving region designed and configured to receive a biological tissue specimen undergoing processing to create a processed specimen for examination; an acoustic pressure wave/shock wave (APW/SW) system that includes at least one APW/SW generator designed, configured, and located relative to the tissue-specimen receiving region, so as to apply at least one APW/SW to the biological tissue specimen; and a control system designed and configured to control the APW/SW system in a predetermined manner that provides an improvement to the processed specimen that would not exist without the application of the at least one APW/SW to the biological tissue specimen.

In still another implementation, the present disclosure is directed to a system that includes a tissue-specimen receiving region containing a biological tissue specimen undergoing processing to create a processed specimen for examination; an acoustic pressure wave/shock wave (APW/SW) system that includes at least one APW/SW generator designed, configured, and located relative to the tissue-specimen receiving region, so as to apply at least one APW/SW to the biological tissue specimen; and a control system designed and configured to control the APW/SW system in a predetermined manner that provides an improvement to the processed specimen that would not exist without the application of the at least one APW/SW to the biological tissue specimen.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein.

DETAILED DESCRIPTION

The present inventors have identified that what is much needed are effective methods for improving, among other things, known histotechnology procedures for processing tissue specimens/sections for microscopic examination (including washing, fixing, dehydrating, hydrating, clearing, embedding, mounting, cryoprotecting, and/or staining tissue specimens/sections, removing embedding medium from tissue specimens/sections, and/or processing tissue specimens/sections with histochemistry, immunohistochemistry, fluorescence immunohistochemistry/immunofluorescence, in situ hybridization and/or fluorescence in situ hybridization for microscopic examination). In this connection, the present inventors have discovered that histotechnological and other processes involving biological tissue can be enhanced by applying one or more acoustic pressure waves/shock waves (APWs/SWs) at one or more, or all, steps of each process.

Improvements spawned by various aspects of methods disclosed herein can include any one or combination of: reducing the time required to perform one or more, or all, steps of the procedures; reducing the amount of media, chemicals, dyes, antibodies and/or antibody mimetics, and/or labeled DNA and/or RNA strands necessary to perform one or more, or all, steps of the procedures; increasing the penetration depth of dyes, antibodies and/or antibody mimetics, and/or labeled DNA and/or RNA strands into the thickness of tissue specimens/sections; reducing the amount of dyes, antibodies and/or antibody mimetics, and/or labeled DNA and/or RNA strands necessary to achieve adequate staining and/or labeling of tissue specimens/sections for microscopic examination; and improving the quality of tissue specimens/sections for use, such as better preservation of the tissue, improved clarity and detectability of microscopic details when examining tissue specimens/sections under a microscope, and/or reduction of fainting of the staining and/or labeling when storing tissue specimens/sections.

Figure 1:
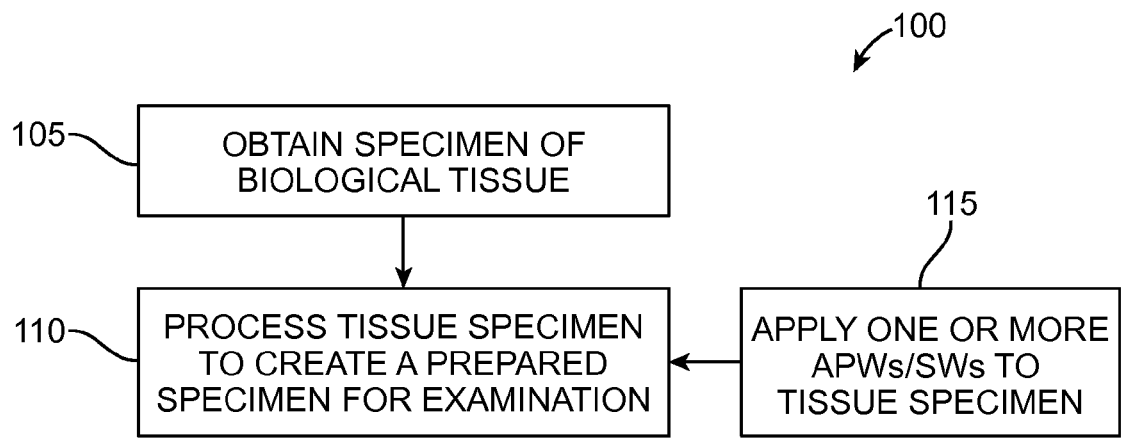
FIG. 1 is a flow diagram illustrating a biological-tissue-processing method for preparing a tissue specimen for examination, the method including subjecting the tissue specimen to one or more acoustic pressure waves/shock waves (APWs/SWs)

Accordingly, some aspects of the present invention are directed to processes implementing such APW/SW enhancements. For example, FIG. 1 illustrates a biological-tissue-processing method 100 of the present invention. Method 100 is used to process biological tissue, such as human, animal, and plant tissue, into a processed specimen that is suitable for examination, such as microscopic examination. At step 105, a specimen of biological tissue is obtained from a suitable source. As described below, the source of the biological tissue can be virtually any source of biological tissue, including any living or dead source. As one example, in the context of living humans, the specimen can be taken from any suitable part of a human body, for example, during a biopsy performed during a surgical event. Many other examples are provided below.

Figure 3:
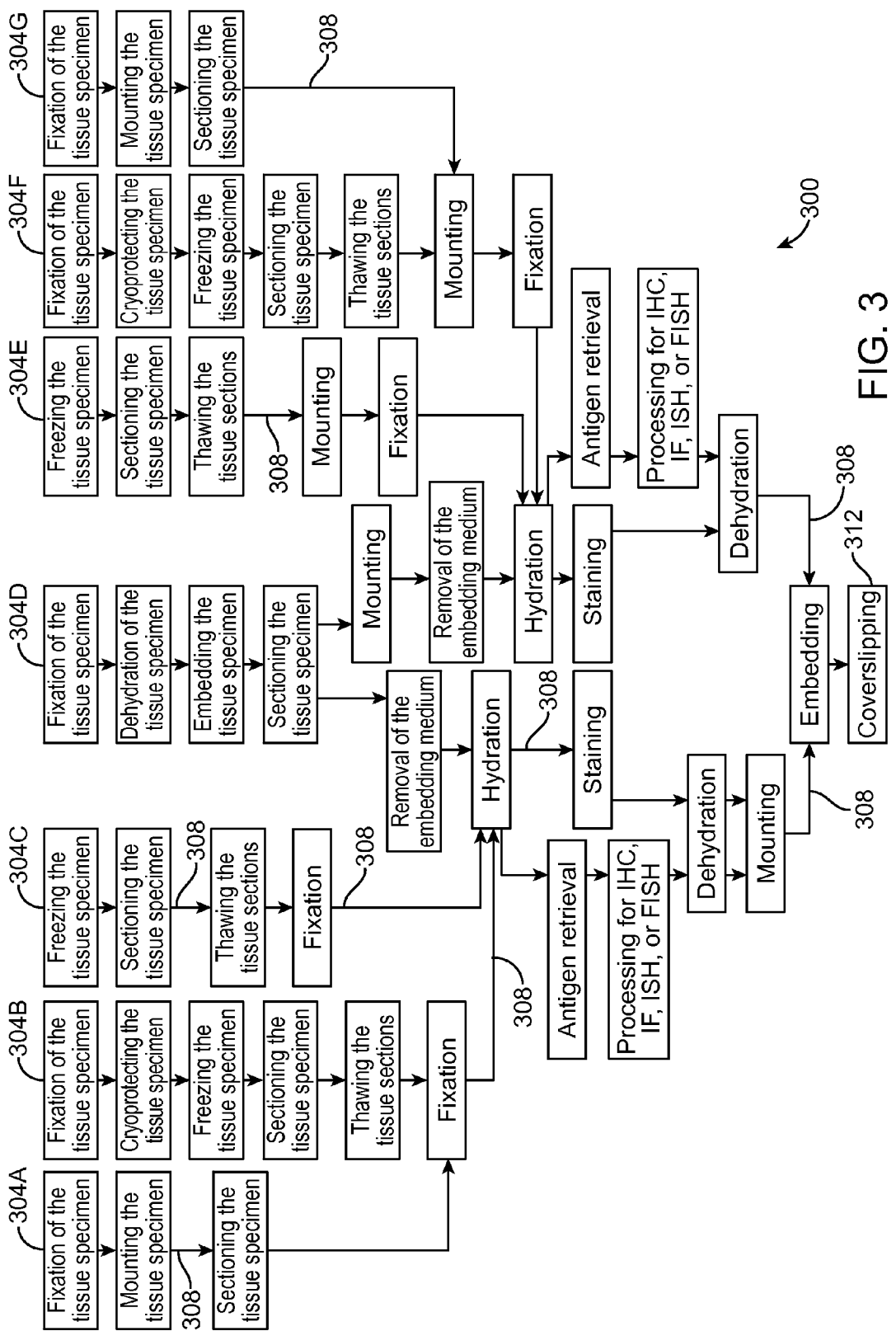
FIG. 3 is an aggregated flow diagram illustrating a number of exemplary histotechnological methods for processing a biological tissue specimen for microscopic examination, each of the methods including subjecting the specimen to one or more APWs/SWs.

At step 110, the tissue specimen is processed in a manner that results in a processed specimen ready for examination. In a histological example where microsconic examination is a goal, specific sub-steps performed during step 110 are myriad and varied. Indeed, aggregated flow diagram 300 of FIG. 3 provides a large number of examples of histotechnological sub-steps that can be performed at step 110 of method 100 to prepare a tissue specimen for examination. That said, other processing steps can be performed at step 110, as well.

At step 115, the tissue specimen is subjected to one or more APWs/SWs. As mentioned above, subjecting the tissue specimen to one or more APWs/SWs can provide any one or more of a number of improvements relative to method 100 being performed without step 115, i.e., fully processing the tissue specimen but without subjecting the tissue specimen to at least one APW/SW. As one example, in the context of the biopsy example provided above, a result of step 115 may be a significant reduction in the amount of time it takes to process the tissue sample into an examinable form. For example, often tissue is excised from a patient in one surgical event, and then the tissue is processed to an examinable state, such as a histological state. Since traditional histotechnological processing takes a relatively long period of time, if the results of the biopsy indicate that further surgical measures, such as excision of cancerous tissue, are required, those additional measures are taken during a second surgical event that takes place typically a day or more after the initial biopsy. However, subjecting the excised tissue specimen to one or more APWs/SWs, as at step 115 of method 100, may allow results of the biopsy to be rendered so quickly that, if further surgical measures are needed, they can be taken within the same surgical event in which the biopsy was performed. This would be a significant improvement to the quality and speediness of patient care. Other examples of improvements brought about by subjecting the tissue sample to one or more APWs/SWs are provided below.

As will be seen from reading this entire disclosure, the application of one or more APWs/SWs at step 115 can be performed in any of a variety of ways. In addition, it is noted that the application of one or more APWs/SWs at step 115 can occur in conjunction with any one or more suitable sub-steps within step 110 of method 100. For each such step for which APW/SW application is indicated, the subjecting of the sample to the one or more APWs/SWs can occur prior to the performance of the sub-step, during the performance of the sub-step, or after the performance of the sub-step, or any combination of these. As those skilled in the art are aware, the effectiveness of the APW/SW application can vary depending upon a number of factors, including the time, relative to the performance of the corresponding sub-step, of the application, the duration of the application, and the characteristics of the APW(s)/SW(s) applied. Various characteristics of APWs/SWs are described in detail below.

In other aspects, the present invention is directed to apparatuses and systems that can be used in or to carry out such enhanced processes. Examples of these and other aspects of the present invention are described below in detail. However, prior to describing examples, a general background of APWs/SWs and a few working definitions are first provided to give the reader a sense of context and an appreciation for the wide applicability of the myriad aspects of the present invention.

Figure 2:
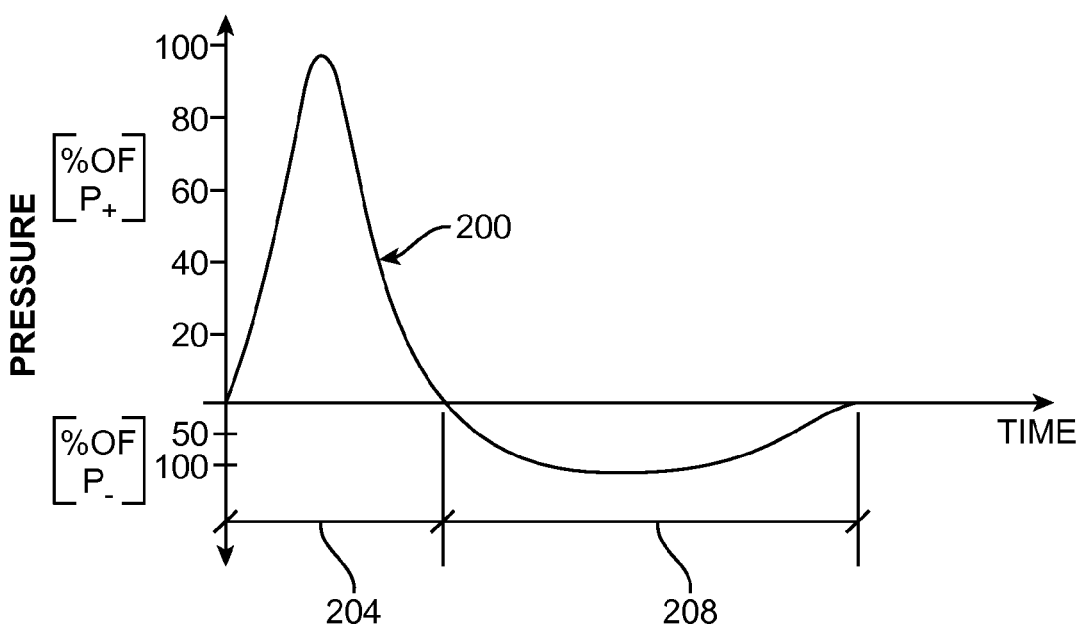
FIG. 2 is a graph of pressure versus time illustrating the pressure profile of a typical APW/SW that can be used, for example, in the tissue-processing method of FIG. 1.

Acoustic pressure waves/shock waves are a type of acoustic energy resulting from any of a variety of phenomena such as, but not limited to, an explosion, lightning, and impacting a target by a bullet, that create a sudden intense change in pressure. As those skilled in the art are aware, an exact, generally accepted definition of the term "acoustic pressure wave/shock wave" does not exist. However, the intense changes in pressure of APWs/SWs produce strong waves of energy that can travel through any elastic medium, such as air, water, biological soft tissue, or certain solid substances such as bone. A fundamental difference between APWs/SWs and ultrasound is that APWs/SWs can be generated and applied as a single acoustic incident having one or only a very few number of wave trains, whereas the ultrasound is understood as a continuous wave form in a frequency range >20 KHz. As those skilled in the art will also appreciate, the fact that APWs/SWs can be generated and applied in a repetitive manner and, thus, with a certain repetition frequency (number of acoustic waves per unit of time) must not be confused with the frequency of ultrasound that is a determining feature of the latter kind of acoustic waves. Referring to FIG. 2, which illustrates a typical APW/SW 200, an APW/SW is characterized by a short-duration compressive phase 204 (positive pressure) followed by a tensile phase 208 (negative pressure). Next to explosions and lightning, several systems have been described to generate APWs/SWs, such as electrohydraulic APW/SW generators (e.g., U.S. Pat. No. 3,942,531 to Hoff and Behrendt, issued on Mar. 9, 1976), electromagnetic APW/SW generators (e.g., German Pat. No. DE 3,312,014 to Eisenmenger, issued on Oct. 11, 1984; U.S. Pat. No. 4,905,675 to Oppelt, issued on Mar. 6, 1980; U.S. Pat. No. 4,901,709 to Rattner, issued on Feb. 20, 1990), piezoelectric APW/SW generators (e.g., U.S. Pat. No. 5,111,805 to Jaggy et al., issued on May 12, 1992), and ballistic APW/SW generators (e.g., U.S. Pat. No. 4,727,875 to Dory, issued on Mar. 1, 1988; U.S. Pat. No. 6,413,230 to Haupt et al., issued on Jul. 2, 2002). The aforementioned Hoff and Behrendt, Eisenmenger, Oppelt, Rattner, Jaggy et al., Dory, and Haupt et al. patents are incorporated herein by reference for their descriptions of APW/SW generators and their operation.

As those skilled in the art will appreciate, APWs/SWs generated with electrohydraulic, electromagnetic, and piezoelectric APW/SW generators are usually convergent/focused, whereas ballistic APWs/SWs are usually divergent/radial. However, divergent/radial APWs/SWs can also be generated using a variety of other methods, some of which are described in U.S. Pat. No. 7,601,127 to Schultheiss et al., issued on Oct. 13, 2009. Divergent/radial APWs/SWs can also be generated by explosions. Vice versa, the technology described in the aforementioned Haupt et al. patent can also be used to generate planar, near planar, and convergent/focused APWs/SWs. An example how to facilitate this is described in U.S. Pat. No. 8,034,004 to Menne et al., issued on Oct. 11, 2011. Other examples in this regard comprise the use of one or more acoustic lenses. The aforementioned Haupt et al., Schultheis s et al., and Menne et al. patents are incorporated herein by reference for their descriptions of APW/SW generators and their operation.

As those skilled in the art will further appreciate, characteristic features of APWs/SWs suitable for use in connection with the present invention include: the positive peak pressure, $P_+$; the negative peak pressure, $P_-$; the rise time, $T_r$, which is the time interval between the points in time at which 10% of $P_+$ and 90% of $P_+$ are reached during the rise in positive pressure; the time period used to calculate the positive energy of an APW/SW, $I_+$, which is the time interval between the point in time at which 10% of $P_+$ is reached during the rise in positive pressure and the point in time at which 10% of $P_+$ is reached during the decline in positive pressure; the time period used to calculate the total energy of an APW/SW, I, which is the time interval between the point in time at which 10% of $P_+$ is reached during the rise in positive pressure and the point in time at which the pressure reaches 10% of $P_-$ at the end of the phase of negative pressure before the pressure finally returns to ambient pressure; the positive energy flux density, $EFD_+$, which is the APW/SW energy transmitted through a certain area within the three-dimensional pressure distribution of an APW/SW during the time period, $I_+$; and the total energy flux density, EFD, which is the APW/SW energy transmitted through a certain area within the three-dimensional pressure distribution of an APW/SW during the time period, I.

In addition to using the foregoing features to characterize APWs/SWs suitable for use in connection with various aspects of the present invention, for the purposes of this disclosure several important terms are defined as follows for use herein and in any denendent claims.

The term "biological tissue" refers to: single cells from humans and animals, such as red blood cells or one or more human or animal cells grown ex vivo in a cell culture; single cells from plants, such as one or more plant cells grown ex vivo in a cell culture; organ parts from humans and animals consisting of more than one cell and, thus, of one or more types of cells, such as a tissue sample or tissue section, collected during a biopsy, during surgery, or post mortem, or grown in a tissue culture; plant parts consisting of more than one cell, such as a leaf from a tree, and sections thereof; entire organs from humans and animals, such as a heart, kidney, brain, or liver, collected during an excisional biopsy, during surgery, or post mortem, and sections thereof; organ systems from humans and animals, such as the gastrointestinal system or the genitals, collected during an excisional biopsy, during surgery, or post mortem, and sections thereof; body parts from humans and animals such as a head, arm, hand, leg or foot, or parts of such body parts, collected during surgery or post mortem, or separated from a human or animal body by an accident, and sections thereof; plant parts such as a branch or root from a tree, and sections thereof; entire human and animal bodies, such as a human body destined for post mortem autopsy in a pathology or forensic medicine lab, or an animal body destined for examination as part of a scientific experiment, and sections thereof; and entire plants such as a flower or a tree. As those skilled in the art will appreciate, the present description of the term "biological tissue" is intended in an illustrative rather than in a limiting sense.

The term "processing biological tissue for microscopic examination" collectively refers to methods known in the art such as: washing a biological tissue sample (henceforth referred to as "tissue specimen") with a medium, such as tap water, distilled water, and/or buffer; fixing a tissue specimen with a fixative, such as formaldehyde, acetone, and/or other chemicals; dehydrating a tissue specimen with a medium, such as alcohol; hydrating a tissue specimen with a medium, such as water; clearing a tissue specimen with a clearing medium, such as xylene; embedding a tissue specimen into an embedding medium, such as paraffin, methacrylate, or polyethylene glycol; mounting a tissue specimen with a mounting medium, such as celloidin; cryoprotecting a tissue specimen with a medium, such as sucrose solution; freezing a tissue specimen with a freezant, such as liquid nitrogen or isopentane cooled down with dry ice; sectioning a tissue specimen with a cutting device, such as a tissue slicer, tissue chopper, microtome, ultramicrotome, vibratome, sliding microtome, tetrander sliding microtome, cryostat, or cryomicrotome; thawing a tissue section; washing a tissue section with a medium, such as tap water, distilled water, and/or buffer; fixing a tissue section with a fixative, such as formaldehyde, acetone, and/or other chemicals; removing embedding medium from a tissue section with a medium, such as alcohol; removing mounting medium from a tissue section with a medium, such as water; dehydrating a tissue section with a medium such as alcohol; hydrating a tissue section with a medium, such as water; mounting a tissue section on a slide suitable for microscopic examination, such as a glass slide; embedding a tissue section into an embedding medium, such as one or more synthetic resins or glycerine; staining a tissue specimen/section with one or more dyes, such as hematoxylin and/or eosin in order to give contrast to the tissue and to highlight particular features of interest; processing a tissue specimen/section with histochemistry, which refers to staining a tissue specimen/section with the underlying mechanistic chemistry understood; processing a tissue specimen/section with immunohistochemistry (IHC) and/or fluorescence immunohistochemistry/immunofluorescence (IF) in order to detect one or more antigens, such as proteins within the tissue specimen/section, by exploiting the principles of antibodies and/or antibody mimetics binding specifically to antigens in biological tissues, including the specific processes known in the art for IHC and IF for sample preparation; sample labeling with primary, secondary and/or tertiary monoclonal and/or polyclonal antibodies, and/or with antibody mimetics, such as affibody molecules, affilins, affitins, anticalins, avimers, DARPins, fynomers, Kunitz domain peptides, and/or monobodies, and/or sample counterstaining, and/or processing a tissue specimen/section with in situ hybridization (ISH) and/or fluorescence in situ hybridization (FISH) in order to localize a specific DNA or RNA sequence within the tissue specimen/section by exploiting the principles of hybridization of labeled complementary DNA or RNA strands to the specific DNA or RNA sequences, including the specific processes known in the art for ISH and FISH for sample preparation, sample labeling, and/or sample counterstaining, as well as any conceivable combination of one or more of these methods. As those skilled in the art will appreciate, the present description of the term "processing biological tissue for microscopic examination" is intended in an illustrative rather than in a limiting sense.

The term "microscopy" collectively refers to all kinds of microscopy known in the art such as: bright field microscopy; dark field microscopy; fluorescence microscopy; confocal laser scanning microscopy; spinning disc confocal microscopy; digital microscopy; fluorescence interference contrast microscopy; phase contrast microscopy; x-ray microscopy; the generation of two-dimensional and three-dimensional virtual slides with slide scanners and special microscope setups; stereo microscopy; transmission electron microscopy; stimulated emission depletion microscopy; photoactivated localization microscopy; stochastic optical reconstruction microscopy; fluorescence resonance energy transfer microscopy; and to all kinds of scanning probe microscopy, such as atomic force microscopy, ballistic electron emission microscopy, electrostatic force microscopy, electrochemical scanning tunneling microscopy, force modulation microscopy, kelvin probe force microscopy, magnetic force microscopy, magnetic resonance force microscopy, scanning near-field scanning optical microscopy, piezo force microscopy, photon scanning tunneling microscopy, photothermal microspectroscopy/microscopy, scanning atom probe microscopy, scanning capacitance microscopy, scanning electrochemical microscopy, scanning electron microscopy, scanning gate microscopy, scanning ion-conductance microscopy, spin polarized scanning tunneling microscopy, scanning thermal microscopy, scanning tunneling microscopy, scanning voltage microscopy, scanning Hall probe microscopy, and scanning SQUID microscopy. As those skilled in the art will appreciate, the present description of the term "microscopy" is intended in an illustrative rather than in a limiting sense.

The term "examination" collectively refers to all kinds of examining tissue specimens known in the art, such as: live on-site or off-site/remote imaging of a tissue specimen/section under any kind of microscope; performing live on-site or off-site/remote quantitative-histological analyses of the tissue specimen/section under any kind of microscope, such as morphometric and stereologic analyses; making drawings or tracings from the tissue specimen/section under any kind of microscope using a pencil, a camera lucida setup, and/or any kind of related computer hardware and software, such as manual, semi-automatic and/or fully automatic tracing software; performing any kind of quantitative-histological analyses on the drawings or tracings, such as morphometric and stereologic analyses; performing any kind of image analysis on the drawings or tracings; taking analog and/or digital photomicrographs and/or movies from a tissue specimen/section under any kind of microscope using any kind of analog or digital still camera for photograph acquisition, any kind of analog or digital video camera for motion picture acquisition, and/or any kind of technology known in the art as being used for time-lapse video-microscopy; processing the photomicrographs and/or movies, such as storing them to computer disk, loading them from computer disk, and/or performing any kind of quantitative-histological analyses of the photomicrographs and/or movies, such as morphometric and stereologic analyses; performing any kind of image analysis on the photomicrographs and/or movies; and generating two-dimensional and three-dimensional virtual slides of the tissue specimen/section using any kind of microscope and/or analog or digital slides scanner, with virtual slides being digital copies of sections of biological tissue; processing the virtual slides such as storing them to computer disk, loading them from computer disk; and/or performing any kind of quantitative-histological analyses of the virtual slides such as morphometric and stereologic analyses, and performing any kind of image analysis on the virtual slides. As those skilled in the art will appreciate, the present description of the term "examination" is intended in an illustrative rather than in a limiting sense.

In one aspect, the present disclosure is directed to methods that apply one or more APWs/SWs on one or more tissue specimens/sections for improving one or more, or all, steps of various histotechnology procedures for processing tissue specimens/sections for microscopic examination. Improvements spawned by such a method can comprise any of the improvements mentioned above and any other improvement someone skilled in the art can think about. For example, such a method can: reduce the time necessary to carry out one or more, or all, steps of the histotechnology procedures, typically between 0.000001% and 99.999%; increase the penetration depth of dyes, antibodies, and/or antibody mimetics, and/or labeled DNA and/or RNA strands into the thickness of tissue specimens/sections, typically between 0.000001% and full penetration through the entire thickness of the tissue specimens/sections; reduce the amount of media and/or chemicals necessary to carry out one or more, or all, steps of the procedures (except of dyes, antibodies and/or antibody mimetics, and/or labeled DNA and/or RNA strands), typically between 0.000001% and 100% (i.e., no use of the corresponding media and/or chemicals at all); reduce the amount of dyes, antibodies and/or antibody mimetics, and labeled DNA and/or RNA strands necessary to achieve adequate staining and/or labeling of tissue specimens/sections for microscopic examination, typically between 0.000001% and 99.999%; better preserve the tissue; improve clarity and detectability of microscopic details when examining tissue specimens/sections under a microscope, typically between actually-existing-but-undetectable improvements and clear detectability of structures within tissue specimens/sections with size and/or distance to each other identical to the resolving capacity of the microscope used to examine the tissue specimens or tissue sections; and reduce fainting of a staining and/or labeling when storing tissue specimens/sections, typically between actually-existing-but-undetectable reductions in fainting and only 0.000001% fainting over a storage time of 100 years.

Any one or more of these improvements can be achieved by applying, for example, from one to 100,000 convergent/focused, planar, near planar and/or divergent/radial APWs/SWs before and/or during one or more, or all, steps of histotechnology procedures for processing tissue specimens/sections for microscopic examination. Such waves can have, for example: a constant or variable repetition frequency from, for example, about 0.001 Hz to about 1,000 Hz; a positive peak pressure, $P_+$, from, for example, about +0.000001 MPa to about +1,000 MPa relative to ambient pressure; a negative peak pressure, $P-$, from, for example, about -0.000001 MPa to about -1,000 MPa relative to ambient pressure; a positive energy flux density, EFD+, at the location of $P_+$ from, for example, about 0.000001 $mJ/mm^2$ to about 100 $mJ/mm^2$; a total energy flux density, EFD, at the location of $P_+$ from, for example, about 0.000002 $mJ/mm^2$ to about 200 $mJ/mm^2$; a rise time, $T_r$, from about one nanosecond to about 250 microseconds; a time interval used to calculate the positive energy of the APW/SW, $I_+$, from, for example, about two nanoseconds to about 500 microseconds; and a time interval used to calculate the total energy of the APW/SW, I, from, for example, about three nanoseconds to about 1,000 microseconds. The distance between the one or more APW/SW generators applied to generate the APWs/SWs and the tissue specimens/sections in this implementation can range from about 0 mm (with the tissue specimens/sections coupled directly to one or more of the APW/SW generators), to about 1,000 mm. In a case in which the APWs/SWs have one or more points of highest pressure/focal points outside the housing or housings of the one or more APW/SW generators, the tissue specimens/sections can be positioned at any possible position relative to the one or more points of highest pressure/focal points within a distance of, for example, about 0 mm to about 1,000 mm to one or more of the APW/SW generators, including the position or positions of the one or more points of highest pressure/focal points themselves.

In another aspect, the present disclosure is directed to systems that apply APWs/SWs to tissue specimens/sections, and that can include: one or more first containers filled with any first medium known in the art as being used for the processing of tissue specimens and tissue sections for microscopic examination, with the one or more first containers being made from any material known in the art APWs/SWs can propagate through; one or more first adjustment devices for adjusting one or more physico-chemical properties of the first medium; one or more first sensors for measuring the one or more physico-chemical properties of the first medium; one or more second containers filled with any second medium known in the art APWs/SWs can propagate through, with the one or more second containers being made from any material known in the art to achieve the aims of applying APWs/SWs on one or more tissue specimens/sections as outlined relative to the first aspect, above; one or more second adjustment devices for adjusting one or more physico-chemical properties of the second medium; one or more second sensors for measuring the one or more physico-chemical properties of the second medium; and one or more APW/SW generators generating convergent/focused, planar, near planar, and/or divergent APWs/SWs by making use of one or more of the technologies known in the art, such as electrohydraulic APW/SW generators, electroconductive APW/SW generators, electromagnetic APW/SW generators, piezoelectric APW/SW generators, and/or ballistic APW/SW generators, and/or making use of explosions.

It is contemplated that a method that permits the application of APWs/SWs on tissue specimens/sections in connection with processing tissue specimens/sections for microscopic examination will provide several advantages. Such a method, for example, would permit substantial improvements of procedures of histotechnology known in the art, such as the procedures noted above. This advantage is particularly important, considering that application of APWs/SWs on tissue specimens/sections can result, for example, in any one or more of the improvements noted above. Another significant advantage of such a method is that it can reduce the amount of media and/or chemicals necessary to carry out one or more, or all, steps of the procedures of histotechnology. Because many of the media and chemicals are regarded as being toxic, the application of APWs/SWs on tissue specimens/sections in connection with processing tissue specimens/sections for microscopic examination can substantially reduce potential threats not only to the health and life of those lab workers performing the methods for processing biological tissue for microscopic examination, but also to the environment.

It is further contemplated that a system configured to permit the application of APWs/SWs on tissue specimens/sections in connection with processing tissue specimens/sections for microscopic examination would provide several advantages. Such a system, for example, would permit to automate the application of APWs/SWs on tissue specimens/samples during the various sub-steps of histotechnology procedures, such as the sub-steps noted above. This advantage is particularly important considering that the automation of the application of APWs/SWs on tissue specimens/sections in connection with processing tissue specimens/sections for microscopic examination can optimize this process of applying APWs/SWs, and can keep those lab workers performing the methods for processing biological tissue for microscopic examination away from the exposure to APWs/SWs that in itself may pose a potential threat to their health and lives when operated inappropriately.

Referring again to the figures, FIG. 3 is an aggregated flow diagram 300 illustrating a number of exemplary methods of the current invention for applying APWs/SWs in order to improve procedures known in the art for processing tissue specimens for microscopic examination. Full ones of the various methods illustrated can be individually discerned by starting at one of the top blocks 304A to 304G and tracing a path through diagram 300, following the connecting arrow-headed lines 308 (only a few labeled to avoid unnecessary clutter), to coverslipping block 312. As can be readily seen, for any one starting top block 304A to 304G, there are multiple paths through diagram 300. The exemplary methods illustrated in aggregated diagram 300 differ from each other with regard to the way of fixation, embedding, mounting, staining, and processing of tissue specimens/sections cut from the tissue specimens for microscopic examination, as well as with regard to the sequence of performing the different steps of fixation, embedding, mounting, staining, and processing of tissue specimens/sections cut from the tissue specimens for microscopic examination. For each of these steps, several procedures are known in the art, such as fixing a tissue specimen before sectioning with a fixative such as neutral buffered formalin, embedding a tissue specimen in an embedding medium such as paraffin, mounting a tissue specimen in a mounting medium such as celloidin, cryoprotecting a tissue specimen with a suitable means, such as sucrose solution, freezing a tissue specimen before sectioning with a freezant, such as liquid nitrogen or isopentane cooled down with dry ice, mounting a tissue specimen/section before staining on a slide suitable for microscopic examination such as a glass slide, staining a mounted tissue specimen/section with one or more dyes such as hematoxylin and/or eosin, staining a tissue specimen/section freely floating in a liquid (known in the art as free floating sections) with one or more dyes, such as hematoxylin and/or eosin, mounting a tissue specimen/ section after staining on a slide suitable for microscopic examination such as a glass slide, mounting a tissue specimen/section before processing it with IHC, IF, ISH, and/or FISH on a slide suitable for microscopic examination such as a glass slide, processing a mounted tissue specimen/section with IHC, IF, ISH, and/or FISH, processing a tissue specimen/section freely floating in a liquid (known in the art as free floating sections) with IHC, IF, ISH, and/or FISH, and mounting a tissue specimen/section after processing it with IHC, IF, ISH, and/or FISH on a slide suitable for microscopic examination such as a glass slide. Furthermore, processing a tissue specimen/section with IHC, IF, ISH, and/or FISH can include a step of staining the tissue specimen/section with one or more dyes, and IHC can be performed with antibodies and/or antibody mimetics. As those skilled in the art will appreciate, while various aspects of the current invention are described herein by reference to the details of particular exemplary methods as illustrated in FIG. 3, it is to be understood that the disclosure is intended in an illustrative rather than in a limiting sense, as it is contemplated that modifications will readily occur to those skilled in the art, within the spirit of the invention and the scope of the appended claims.

For example, those skilled in the art will understand that depending on what actually shall be achieved with microscopic examination of a tissue specimen/section, one or more steps of any one of the full methods illustrated in aggregated diagram 300, i.e., a method that started with one of top blocks 304A to 304G and ends with coverslipping block 312, can be omitted. For instance, tissue specimens/sections can be dehydrated before or after staining and/or before or after processing with IHC/IF/ISH/FISH and/or before or after mounting, respectively; mounting a tissue specimen/section on a slide suitable for microscopic examination after staining the tissue specimen/section and/or after processing the tissue specimen/ section with IHC, IF, ISH, and/or FISH can be performed with or without dehydration of the tissue specimen/section; and embedding a tissue specimen/section after mounting them on a slide suitable for microscopic examination can be performed with or without dehydration of the tissue specimen/ section. Those skilled in the art will recognize other steps of an entire method of aggregated diagram 300 that can be omitted, added, and/or performed in changed order to suit a particular application. Besides this, certain microscopic techniques, such as dark field microscopy, do not even require staining a tissue specimen/section before microscopic examination. Those skilled in the art will also appreciate that despite the number of different paths through aggregated flow diagram 300, the diagram shown is merely exemplary and does not capture all methods that can benefit from one or more of the APW/SW application schemes disclosed herein. In this connection, though each of the different ways through flow diagram 300 in FIG. 3 includes a step of coverslipping, there are certainly other methods that do not require coverslipping. For example, various types of microscopy performed from beneath a specimen/section do not necessarily require coverslipping. Furthermore, those skilled in the art should appreciate that APW/SW application can occur at any possible time relative to each of the steps depicted in aggregated flow diagram 300, such as prior to one or more, or all, of these steps, during one or more, or all, of these steps, or subsequent to one or more, or all, of these steps.

Figure 4:
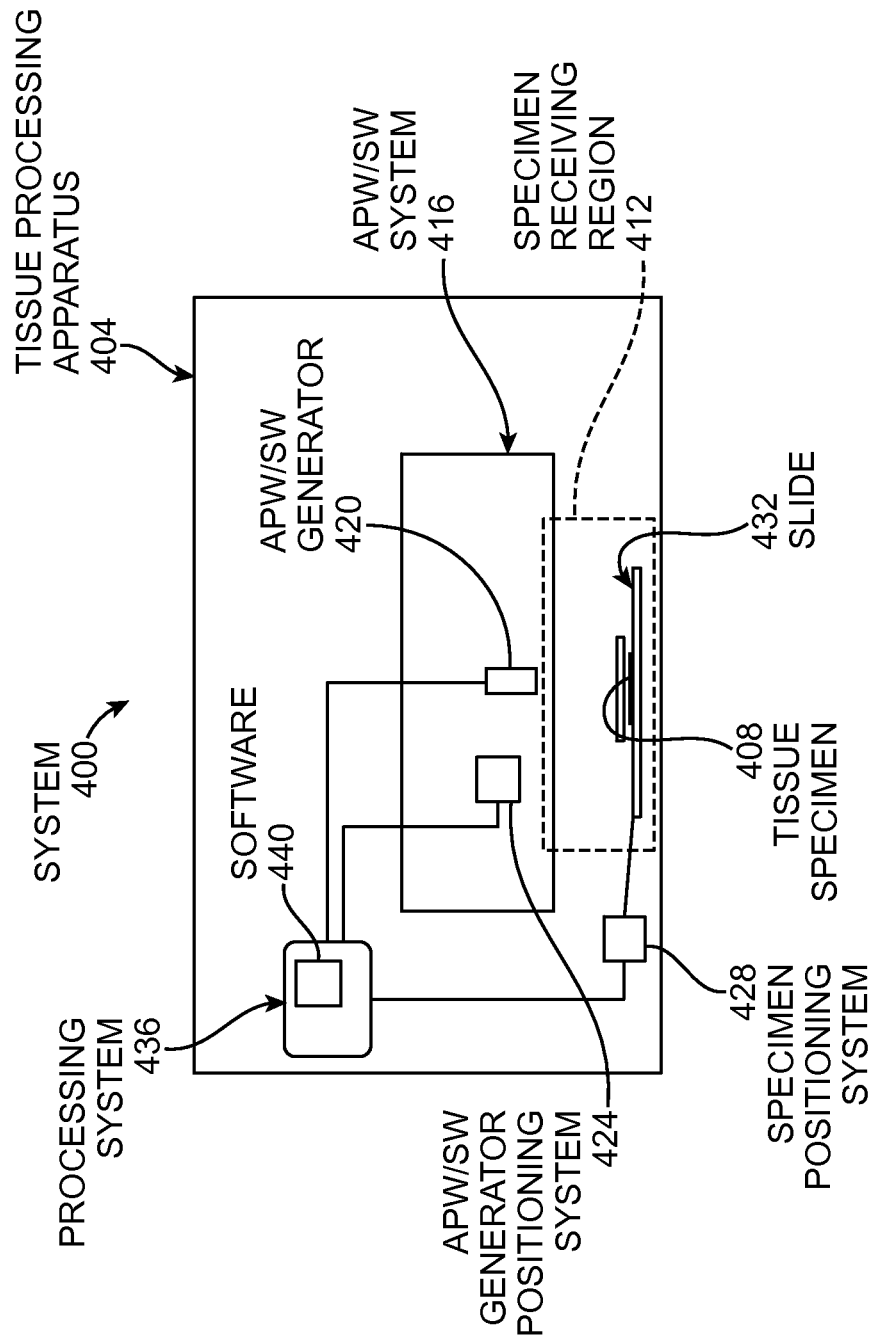
FIG. 4 is a high-level diagram of a system for applying APWs/SWs for improving the processing of a tissue specimen for examination, for example, using the method illustrated in FIG. 1.

FIG. 4 illustrates a system 400 that includes a biological-tissue processing apparatus 404 and a biological tissue specimen 408. Tissue processing apparatus 404 can be designed and configured for performing any one of the methods disclosed herein, including method 100 of FIG. 1 and any one of the methods illustrated in aggregated flow diagram 300 of FIG. 3, as well as other tissue-processing methods that those skilled in the art can think of. Tissue specimen 408 can be any of the biological tissue specimens, samples, sections, etc., disclosed herein, and tissue processing apparatus 404 can be used to achieve any of the improvements disclosed herein and/or any other improvements that a skilled artisan can conceive.

Tissue processing apparatus 404 includes a tissue-specimen receiving region 412 and an APW/SW system 416 for generating and applying one or more APWs/SWs, for example, in any of the manners, at any of the time, and for any of the purposes disclosed herein. APW/SW system 416 comprises one or more APW/SW generators (only one generator 420 shown for ease) that are located, fixedly or movably, relative to specimen receiving region 412 so that apparatus achieves its goal(s) of providing one or more improvements over the performance of like specimen preparation processing, but without utilizing APW/SW energy. APW/SW system 416 can include one or more APW/SW generator positioning systems 424 for positioning/adjusting the position of, the one or more APW/SW generators 420 to achieve the desired results. Each APW/SW generator 420 can be any one of the various generator types disclosed herein.

Tissue processing apparatus 404 can also include a specimen positioning system 428 for properly positioning tissue specimen 408 properly within specimen receiving region 412 and/or for moving the tissue specimen into the specimen receiving region. Such movement may be with or without a carrying container or other carrying member, such as a microscopy slide 432. In this connection, specimen receiving region 412 can be configured in any manner suitable for the type of processing involved. For example, if tissue specimen 408 is provided to specimen receiving region 412 on a microscopy slide 432 (as shown), the specimen receiving region can be specially configured to handle such specimen/slide combination, or a plurality of such combinations. However, in other embodiments, specimen receiving region 412 can be configured to receive an un-mounted tissue specimen, such as the free-floating specimen illustrated in FIG. 5. In such case, specimen receiving region 412 (FIG. 4) can be configured to receive one or more containers containing the free-floating specimen and any suitable/necessary medium.

With continuing reference to FIG. 4, system 400 also includes a processing system 436 designed and configured to control the functioning of tissue processing apparatus 404. Depending on the types of APW/SW system 416, APW/SW generator positioning system 424, and specimen positioning system 428, processing system 436 may control each of these systems based on a suitable user input and/or control scheme. In one example, processing system 436 contains software 440 that is specifically written to carry out one or more special APW/SW dosing schemes that are based on the functionality that system 400 is designed for. For example, these dosing schemes can be based on any one or more of the histotechnological sub-steps disclosed herein in conjunction with the results that are desired to be achieved.

Figure 5:
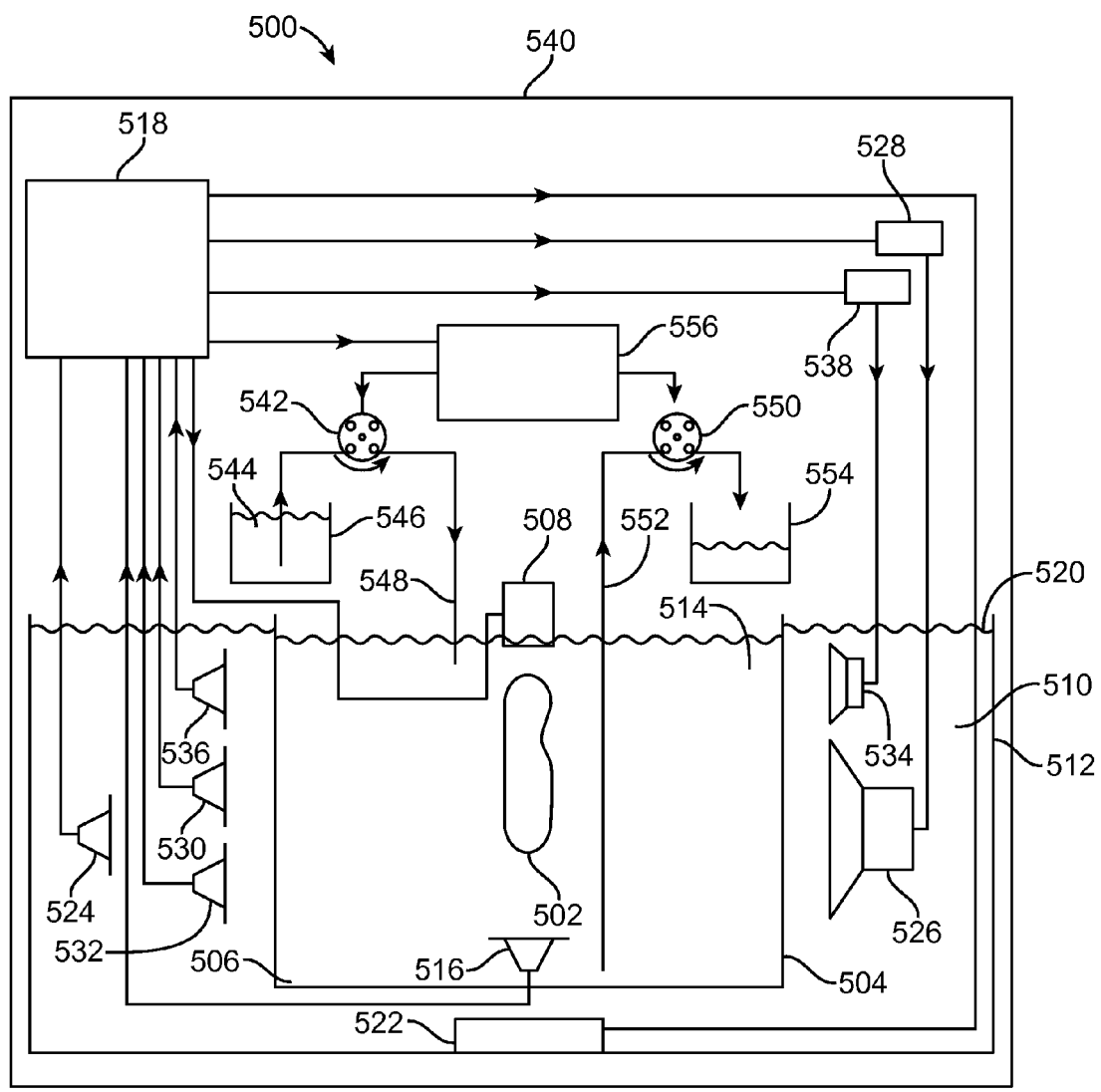
FIG. 5 is a schematic diagram of an exemplary embodiment of the system of FIG. 4.

With the generalities of system 400 of FIG. 4 in mind, FIG. 5 illustrates a specific exemplary system 500 for applying one or more APWs/SWs to one or more tissue specimens (only one tissue specimen 502 shown), for example, in conjunction with any one of the indicated steps of the methods represented in aggregate flow diagram 300 of FIG. 3. As those skilled in the art will readily appreciate, system 500 can be particularly configured to apply APWs/SWs to tissue specimen 502 in accordance with the APW/SW parameters described above and to achieve one or more of the improved results and/or benefits also described above. To provide a sense of scale, particular examples of system 500 can be sized and configured for handing one or more tissue specimens with volumes between, for example, about 1.0 $\mu m^3$ to about 1.0 $m^3$; tissue sections with area typically between 1.0 $\mu m^2$ and 1.0 $m^2$; and tissue specimens and tissue sections having a thickness typically between 0.000001 mm and 1,000 mm.

In system 500, a tissue specimen 502 is located within a first container 504 that is filled with a first medium 506, which can be any medium known in the art as being used for the processing of tissue specimens/sections for microscopic examination. First container 504 can be made from any material known in the art that APWs/SWs can propagate through. Any one or more physico-chemical properties of first medium 506, such as its components, its temperature, its vapor pressure, the amount and kind of one or more gases dissolved in the first medium, the ability of APWs/SWs to induce cavitation in the first medium, and any other physico-chemical property someone skilled in the art can think about, can be adjusted, for example, by means of a first adjustment device 508, which can be a heater, a cooler, a combination of a heater and a cooler, and/or any other device that is known in the art for being used to adjust properly the physico-chemical properties of the first medium. First adjustment device 508 can be positioned either fully or partly (as shown in the illustrated example) within first medium 506 and first container 504, or outside the first medium either fully or partly within the first container, and/or either fully or partly within a second medium 510 contained in a second container 512, or outside the second medium and second container.

First container 504 can have an opening 514 (as shown in the illustrated example) or can be closed, and can be positioned either fully or partly (as shown in the illustrated example) within second medium 510 and second container 512. Any one or more of the physicochemical properties of first medium 506 can be measured by a first sensor 516, which can be positioned either partly or fully (as shown in the illustrated example) within the first medium and/or the first container, or partly or fully within second medium 510 and/or second container 512, or outside the first and second mediums and/or the first and second containers. A central processing unit (CPU) 518 or other machine, can analyze and process the information gathered by first sensor 516, and the CPU can control first adjustment device 508 to adjust one or more of the physico-chemical properties of first medium 506. CPU 518 can control first adjustment device 508 based on settings made by a user before and/or during the application of APWs/SWs on tissue specimen 502. As those skilled in the art will readily appreciate, the user can input settings for system 500 by, for example, pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the system.

Second container 512 can have an opening 520 (as shown in the illustrated example) or can be closed, and can be made of any material known in the art to achieve the aims of applying APWs/SWs on tissue specimen 502 in a suitable manner, such as any of the manners outlined above. Second medium 510 can be, for example, water, gel (such as ultrasound coupling gel), oil (such as castor oil), polyvinyl alcohol solution, or any other medium known in the art that APWs/SWs can propagate through, with or without induction of cavitation. Any one or more physico-chemical properties of second medium 510, such as its components, its temperature, its vapor pressure, the amount and kind of one or more gases dissolved therein, the ability of APWs/SWs to induce cavitation therein, and any other physico-chemical properties someone skilled in the art can think about, can be adjusted by means of a second adjustment device 522, which can be, for example, a heater, a cooler, a combination of a heater and a cooler, and/or any other device that is known in the art for being used to adjust properly the physico-chemical properties of the second medium.

Second adjustment device 522 can be positioned either fully (as shown in the illustrated example) or partly within second medium 510 and/or second container 512, or outside the second medium and/or the second container. Any one or more of the physico-chemical properties of second medium 510 can be measured by a second sensor 524, which can be positioned either partly or fully (as shown in the illustrated example) within the second medium and/or second container 512, or outside the second medium and/or the second container. CPU 518 can analyze and process the information gathered by second sensor 524, and the CPU can control first adjustment device 508 to adjust the physico-chemical properties of first medium 506 and/or second adjustment device 522 to adjust the physico-chemical properties of second medium 510 by processing the information gathered by the second sensor based on settings made by the user before and/or during the application of APWs/SWs on tissue specimen 502.

In this example, system 500 includes an APW/SW generator 526 that can be positioned either fully (as shown here) or partly within second medium 510, or is coupled to the second medium through an opening (not shown) within a wall, and/or the top, and/or the bottom of the second container, for example, in a manner known in the art, with the opening closed with a membrane or another means that APWs/SWs can propagate through. In alternative embodiments, the opening does not need to be closed. The APWs/SWs emitted from APW/SW generator 526 can be, for example, convergent/focused, planar, near planar, or divergent/radial APWs/SWs, as described above, or any possible combination of such APWs/SWs, and can be generated with one or more, or all, types of APW/SW generators described in detail above such as electrohydraulic, electroconductive, electromagnetic, piezoelectric, and/or ballistic APW/SW generators, or by explosions, or any other way known in the art to generate APWs/SWs.

The distance between APW/SW generator 526 and tissue specimen 502 is typically from 0 mm (with the tissue specimen coupled directly to one or more of the APW/SW generators), to 1,000 mm. In case the APWs/SWs have one or more points of highest pressure/focal points outside the housing of APW/SW generator 526, tissue specimen 502 can be positioned at any possible position relative to the one or more points of highest pressure/focal points within a distance from 0 mm to 1,000 mm to the APW/SW generator, including the position or positions of the one or more points of highest pressure/focal points themselves. Improvement of the processing of the tissue specimen for microscopic examination by means of applying APWs/SWs as described above can be achieved with or without induction of cavitation on the surface or within tissue specimen 502. A first control unit 528 can be provided for controlling APW/SW generator 526. By either APW/SW generator 526, first control unit 528, or any possible interplay between the APW/SW generator and the first control unit, the properties of the APWs/SWs can be modified and adjusted, such as $P_+$, $P_-$, $EFD_+$, EFD, $T_r$, $I_+$, I, and other properties of the APWs/SWs, so that their three-dimensional (3D) pressure distribution as a function of (wall clock) time, their repetition frequency, the total number of APWs/SWs applied, as well as any other property of APWs/SWs known in the art, and any possible combination of the properties of APWs/SWs.

Settings on first control unit 528 can be made by the user before and/or during the application of APWs/SWs before and/or during any of the steps suitable for improving the processing of tissue specimen 502 for microscopic examination with APWs/SWs as specified in detail in connection with aggregated flow diagram 300 of FIG. 3, for example, by pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the first control unit. First control unit 528 can also be controlled by CPU 518 or any possible combination of the CPU and the user. At the end of applying, typically from one to 100,000, APWs/SWs before and/or during one or more, or all, steps suitable for improving the processing of tissue specimen 502 for microscopic examination with APWs/SWs as specified in detail above, APW/SW generator 526 can be switched off by the user, first control unit 528, and/or CPU 518.

In this example, a third sensor 530 is provided to measure one or more of the properties, such as $P_+$, $P_-$, $EFD_+$, EFD, $T_r$, $I_+$, I, the 3D pressure distribution as a function of (wall clock) time, and other properties of those parts of the APWs/SWs that reach tissue specimen 502. Third sensor 530 can be positioned, for example, in front of, within, or behind (as shown in the illustrated example) the tissue specimen and, thus, either between APW/SW generator 526 and first container 504 within second medium 510 and second container 512, within first medium 506 and the first container, or (as shown in the illustrated example) behind the first container within the second medium and the second container, or outside the first and second containers. CPU 518 can be used to analyze and process the information gathered by third sensor 530 and to control first adjustment device 508 to adjust the physico-chemical properties of the first medium, second adjustment device 522 to adjust the physico-chemical properties of the second medium, and/or first control unit 528 to control the APW/SW generator to adjust the properties of the APWs/SWs. CPU 518 can control first adjustment device 508, second adjustment device 522, and/or first control unit 528 by processing the information gathered by third sensor 530 based on settings made by the user before and/or during the application of APWs/SWs on tissue specimen 502.

In this example, a fourth sensor 532 is provided for measuring one or more of the properties, such as $P_+$, $P_-$, $EFD_+$, EFD, $T_r$, $I_+$, I, the 3D pressure distribution as a function of (wall clock) time, and other properties of those parts of the APWs/SWs that do not reach tissue specimen 502. Fourth sensor 532 can be positioned, for example, between APW/SW generator 526 and first container 504 within second medium 510 and second container 512, within first medium 506 and first container 504, or (as shown in the illustrated example) behind the first container within the second medium and the second container, or outside the first and second containers. CPU 518 can be used to analyze and process the information gathered by fourth sensor 532 and to control first adjustment device 508 to adjust the physico-chemical properties of first medium 506, second adjustment device 522 to adjust the physico-chemical properties of second medium 510, and/or first control unit 528 to control APW/SW generator 526 to adjust the properties of the APWs/SWs. CPU 518 can control first adjustment device 508, second adjustment device 522, and/or first control unit 528 by processing the information gathered by fourth sensor 532 based on settings made by the user before and/or during the application of APWs/SWs on tissue specimen 502.

As seen in FIG. 5, also in this example a signal-emitting device 534 is provided for measuring one or more physico-chemical properties of tissue specimen 502, such as its density, its translucence, its coloration, and other properties. Signal-emitting device 534 emits a certain signal, such as ultrasound waves to measure the density of the tissue specimen, a laser light beam, and/or a light beam to measure the translucence and/or the coloration of the tissue specimen, or other signals. A fifth sensor 536 is provided to detect any signal(s) emitted by signal-emitting device 534 after having passed through and/or been absorbed, reflected, dispersed, etc., by tissue specimen 502, and thereby being either modified or not modified by the tissue specimen. Fifth sensor 536 can be positioned at any suitable place within first medium 506 and first container 504, second medium 510 and second container 512 (as shown in the illustrated example), and/or outside the first and second containers in order to detect adequately the signal emitted by signal emitting device 534 after passing through and/or being absorbed, reflected, dispersed, etc., by tissue specimen 502.

Signal-emitting device 534 can be controlled, for example, by a second control unit 538. By way of signal emitting device 534, second control unit 538, or any possible interplay between the signal emitting device and the second control unit, the properties of the signal emitted by the signal emitting device, such as the frequency and energy of ultrasound waves, the wave length, intensity, and focusing or dispersion of a laser light beam, the spectrum of wave lengths, intensity, and focusing or dispersion of a light beam, and/or any other property(ies), can be modified and adjusted. Settings on second control unit 538 can be made by the user before and/or during the application of APWs/SWs before and/or during any of the steps suitable for improving the processing of the tissue specimen for microscopic examination with APWs/SWs as specified, for example, in detail in connection with aggregated flow diagram 300 of FIG. 3, via any suitable means, such as by pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the second control unit.

Second control unit 538 can also be controlled by CPU 518 or any possible combination of the CPU and the user. Signal-emitting device 534 can be switched on and off at any suitable point in time before, during, and/or after the application of APWs/SWs before and/or during any of the steps suitable for improving the processing of the tissue specimen for microscopic examination with APWs/SWs as specified in detail, for example, in connection with aggregated flow diagram 300 of FIG. 3. CPU 518 can be used to analyze and process the information gathered by fifth sensor 536, and to control first adjustment device 508 to adjust the physico-chemical properties of first medium 506, second adjustment device 522 to adjust the physico-chemical properties of second medium 510, and/or first control unit 528 to control APW/SW generator 526 to adjust the properties of the APWs/SWs. CPU 518 can control first adjustment device 508, second adjustment device 522, and/or second control unit 538, for example, by processing the information gathered by fifth sensor 536 based on settings made by the user on the CPU before and/or during the application of APWs/SWs on tissue specimen 502. In the embodiment shown, one or all components of system 500 are mounted in a housing 540, but they need not be in other embodiments.

In this example, system 500 further includes a first pump 542 for pumping any medium 544 suitable for processing tissue specimen 502 for microscopic examination, such as any one or more, or all, of the media outlined in detail in connection with aggregated flow diagram 300 of FIG. 3, can be pumped from a third container 546 through a first conduit system 548 into first container 504. By means of a second pump 550, any medium 506 suitable for processing tissue specimen 502 for microscopic examination, such as any one or more, or all, of the media outlined in detail in connection with aggregated flow diagram 300 of FIG. 3, can be pumped from first container 504 through a second conduit system 552 into a fourth container 554. By means of first pump 542, first conduit system 548, second pump 550, and second conduit system 552, the process of consecutive exposing the tissue sample to different media for the processing of tissue specimen 502 for microscopic examination, such as any one or more, or all, of the media outlined in detail in connection with aggregated flow diagram 300 of FIG. 3, can be automated fully or in part without need to move tissue specimen 502 and first container 504.

First pump 542 and second pump 550 can be controlled, for example, by a fourth control unit 556. Settings on fourth control unit 556 can be made by the user before, during, and/or after any of the steps for the processing of tissue specimen 502 for microscopic examination, such as steps specified in detail in connection with aggregated flow diagram 300 of FIG. 3, by, for example, pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the fourth control unit. Fourth control unit 556 can also be controlled by CPU 518 and, thus, control can also be based on the information gathered by first sensor 516, second sensor 524, third sensor 530, fourth sensor 532, and/or fifth sensor 536 that is analyzed and processed by the CPU, or any possible combination of the CPU and the user. First pump 542 and second pump 550 can be switched on and off at any suitable point in time before, during, and/or after any of the steps for the processing of tissue specimen 502 for microscopic examination, such as the steps specified in detail in connection with aggregated flow diagram 300 of FIG. 3.

System 500 of FIG. 5 can also include a first motorized position adjustment system (not shown) to adjust the position of each of: tissue specimen 502; first container 504 filled with first medium 506; first adjustment device 508; second medium 510; second container 512; first sensor 516; CPU 518; second adjustment device 522; second sensor 524; APW/SW generator 526; third sensor 530; fourth sensor 532; signal emitting device 534; and fifth sensor 536. One or many, or all, components of first position adjustment system can be motorized, but they need not be in other embodiments. In this example, the first motorized position adjustment system is designed and configured to freely adjust these components in XYZ space with six degrees of freedom each, including lifting and lowering (i.e., parallel to the walls of second container 512 in the example shown here), moving in directions X and Y (i.e., parallel to the bottom of the second container in the example shown here), rotating, and tilting, and any possible combination of these movements in XYZ space in a (wall clock) duration in time typically, but not necessarily, from 0.0001 second to 60 minutes each.

This can be achieved, for example, by separate positioning devices (not shown) attached to and controlled by the first motorized position adjustment system, or senarated from but controlled by the first motorized position adjustment system, and one or more of the positioning devices executing positioning of each of tissue specimen 502, first container 504, first adjustment device 508, second container 512, first sensor 516, second adjustment device 522, second sensor 524, APW/SW generator 526, third sensor 530, fourth sensor 532, signal emitting device 534, and fifth sensor 536. Each of these positioning devices can comprise, for example, one or more: lifters; connecting rods; winches; pivot mountings; and/or other means to achieve individual movements of the corresponding component with six degrees of freedom each. Each of these positioning devices can also contain one or more sensors (not shown) to measure the actual position in XYZ space of the corresponding component.

Based on the input by the sensors, the first motorized position adjustment system can act on positioning the individual positioning devices outlined above using, for example, a closed-loop controller or feedback controller (not shown) to adjust the positions of tissue specimen 502; first container 504 filled with first medium 506; first adjustment device 508; second medium 510; second container 512; first sensor 516; CPU 518; second adjustment device 522; second sensor 524; APW/SW generator 526; third sensor 530; fourth sensor 532; signal emitting device 534; fifth sensor 536, separately or together in suitable grouping(s), freely in XYZ space with six degrees of freedom and with positioning reproducibility typically within a range of 0.0001 µm to 100 mm for each degree of freedom. The first motorized position adjustment system can be controlled by a third control unit (not shown). By either the first motorized position adjustment system, the third control unit, or any possible interplay between the first motorized position adjustment system and the third control unit, the position of each of the tissue specimen 502; first container 504 filled with first medium 506; first adjustment device 508; second medium 510; second container 512; first sensor 516; CPU 518; second adjustment device 522; second sensor 524; APW/SW generator 526; third sensor 530; fourth sensor 532; signal emitting device 534; and fifth sensor 536 can be modified and adjusted freely in XYZ space with six degrees of freedom before and/or during the application of APWs/SWs before and/or during any of the steps suitable for improving the processing of the tissue specimen for microscopic examination with APWs/SWs, for example, as specified in detail in connection with aggregated flow diagram 300 of FIG. 3.

Settings on the third control unit can be made by the user before and/or during the application of APWs/SWs before and/or during any of the aforementioned processing steps, for example, by pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the third control unit. The third control unit can also be controlled by CPU 518 and, thus, also based on the information gathered by first sensor 516, second sensor 524, third sensor 530, fourth sensor 532, and/or fifth sensor 536 that can be analyzed and processed by the CPU, or any possible combination of the CPU and the user. The first motorized position adjustment system can be switched on and off at any suitable point in time before, during, and/or after the application of APWs/SWs before and/or during any of the processing steps described or mentioned above.

System 500 of FIG. 5 may also contain a second motorized position adjustment system (not shown), that can be used to move first container 504 with tissue specimen 502 and first medium 506 through an opening (not shown) in one or more walls and/or the top and/or the bottom of housing 540 into and out of the housing in a (wall clock) duration in time, typically, though not necessarily, between 0.0001 second and 60 minutes. One or many, or all, components of the second position adjustment system can be motorized, but they need not be in other embodiments. The second motorized position adjustment system can comprise, for example, lifters, connecting rods, winches, pivot mountings, drawers, and/or other means to move first container 504 with tissue specimen 502 and first medium 506 into and out of housing 540. Also by means of the second motorized position adjustment system, first container 504 with tissue specimen 502 and first medium 506 can be placed adequately within system 500 to apply APWs/SWs on the tissue specimen without exposing any part of the body of the user, such as fingertips, fingers, hands, arms, hair, beard, or any other part of body of the user, and/or any part of her clothing and/or accessories, such as bracelets, necklaces, ties, scarves, or any other part of her clothing/accessories, to APWs/SWs before, during, and/or after any of the steps for processing the tissue specimen, as specified in detail in connection with aggregated flow diagram 300 of FIG. 3.

The second motorized position adjustment system can be controlled by a fifth control unit (not shown). Settings on the fifth control unit can be made by the user before, during, and/or after any of the steps of processing tissue specimen 502 for microscopic examination, such as any one or more, or all, of the steps specified in detail in connection with aggregated flow diagram 300 of FIG. 3, for example, by pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the fifth control unit. The fifth control unit can also be controlled by CPU 518 and, thus, control can also be based on the information gathered by first sensor 516, second sensor 524, third sensor 530, fourth sensor 532, and/or fifth sensor 536 that is analyzed and processed by the CPU, or any possible combination of the CPU and the user. The second motorized position adjustment system can be switched on and off at any suitable point in time before, during, and/or after any of the steps for processing tissue specimen 502.

Instead of tissue specimen 502, first container 504 filled with first medium 506 can contain a tissue section (not shown) cut from a tissue specimen, such as specimen 502, and mounted on a slide (not shown) suitable for microscopic examination, such as a glass slide. First container 504 filled with first medium 506 can also contain a tissue section (not shown) cut from a tissue specimen, such as specimen 502, that is not mounted on a slide suitable for microscopic examination, known as a free-floating section.

As those skilled in the art will appreciate, it is contemplated that an almost infinite number of modifications can be made to the system disclosed herein for applying APWs/SWs on tissue specimens/sections in connection with processing tissue specimens/sections for microscopic examination, for example, by varying the number and/or type of components of system 500 particularly illustrated, respectively, in FIG. 5, and those components mentioned above that are not shown in FIG. 5.

With regard to the aforementioned possible variations of systems made in accordance with the present invention for applying APWs/SWs for improving the processing of a tissue specimen/section for microscopic examination, for example, as specified in detail in connection with aggregated flow diagram 300 of FIG. 3, a possible modification of system 500 of FIG. 5 is the same as that system, with the exception that the modified system includes only tissue specimen/section 502, second medium 510 contained in second container 512, APW/SW generator 526, and first control unit 528. Alternatively, second container 512 can contain first medium 506.

Also with regard to the aforementioned possible variations of systems made in accordance with the present invention for applying APWs/SWs for improving the processing of a tissue specimen/section for microscopic examination, for example, as specified in detail in connection with aggregated flow diagram 300 of FIG. 3, another possible modification (not shown) of system 500 of FIG. 5 is the same as that system, with the exception that a tissue specimen/section is placed within a container that can be made of any material that achieves the goal of applying APWs/SWs on tissue specimen/section, for example, for any one or more of the purposes described above. The container is filled with a medium that can be any medium known in the art as being used for the processing of tissue specimens/sections in accordance with the present invention. The container can have an opening or can be closed. An APW/SW generator is positioned either fully or partly within the medium, or is coupled to the medium through an opening within a wall, and/or the top, and/or the bottom of the container in a suitable manner, such as with the opening closed with a membrane or another means that APWs/SWs can propagate through. Alternatively, the opening need not be closed, as those skilled in the art will appreciate. The APW/SW generator can be controlled by a control unit. By means of the APW/SW generator, the control unit, or any possible interplay between the APW/SW generator and the control unit, the properties of the APWs/SWs, such as $P_+$, $P_-$, $EFD_+$, $EFD_-$, $T_r$, $I_+$, I, and other properties of the APWs/SWs, such as their three-dimensional (3D) pressure distribution as a function of (wall clock) time, their repetition frequency, the total number of APWs/SWs applied, as well as any other property of APWs/SWs known in the art, and any possible combination of the properties of APWs/SWs, can be modified and adjusted. Settings on the control unit can be made by the user before and/or during the application of APWs/SWs to the tissue specimen/section before and/or during any of the steps suitable for improving the processing of the tissue specimen/section for microscopic examination with APWs/SWs, for example, as specified in detail in connection with aggregated flow diagram 300 of FIG. 3, for example, by pushing buttons, adjusting knobs, operating a touchscreen, adjusting devices known in the art as dip switches and jumper boxes, entering code via a keyboard, using a computer mouse and/or a trackball, operating a foot pedal, voice control, gesture recognition, or any other possible interaction between the user and the control unit. At the end of applying typically from one to 100,000 APWs/SWs before and/or during one or more, or all, steps suitable for improving the processing of the tissue specimen/section, the APW/SW generator can be switched off by the user and/or the control unit.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of processing biological tissue for microscopic examination, the method comprising:
   obtaining a tissue specimen from the biological tissue;
   processing the tissue specimen so as to prepare a processed specimen for examination; and
   subjecting the tissue specimen to at least one acoustic pressure wave/shock wave (APW/SW) so as to provide an improvement in 1) said processing, 2) a result of at least one procedures used in said processing, and/or 3) an aspect of the processed specimen, relative to the method being performed without said subjecting the tissue specimen to the at least one APW/SW.

2. A method according to claim 1, wherein said processing the tissue specimen includes histotechnologically processing the tissue specimen for microscopic examination.

3. A method according to claim 2, wherein said processing includes utilizing an amount of an additive and said subjecting the tissue specimen to at least one APW/SW reduces the amount of the additive needed relative to performing the method without said subjecting the tissue specimen to the at least one APW/SW.

4. A method according to claim 3, wherein said utilizing includes utilizing an amount of a fixative.

5. A method according to claim 3, wherein said utilizing includes utilizing an amount of a washing medium.

6. A method according to claim 3, wherein said utilizing includes utilizing an amount of an embedding and/or mounting medium.

7. A method according to claim 3, wherein said utilizing includes utilizing an amount of an additive for staining and/or labeling.

8. A method according to claim 7, wherein said utilizing includes utilizing an amount of a dye.

9. A method according to claim 7, wherein said utilizing includes utilizing an amount of antibodies.

10. A method according to claim 7, wherein said utilizing includes utilizing an amount of antibody mimetics.

11. A method according to claim 7, wherein said utilizing includes utilizing an amount of labeled DNA strands.

12. A method according to claim 7, wherein said utilizing includes utilizing an amount of labeled RNA strands.

13. A method according to claim 2, wherein said processing takes an amount of time, and said subjecting the tissue specimen to at least one APW/SW reduces the amount of time relative to performing the method without said subjecting the tissue specimen to the at least one APW/SW.

14. An apparatus, comprising:
    a tissue-specimen receiving region designed and configured to receive a biological tissue specimen undergoing processing to create a processed specimen for examination;
    an acoustic pressure wave/shock wave (APW/SW) system that includes at least one APW/SW generator designed, configured, and located relative to said tissue-specimen receiving region, so as to apply at least one APW/SW to the biological tissue specimen; and
    a control system designed and configured to control said APW/SW system in a predetermined manner that provides an improvement to the processed specimen that would not exist without the application of the at least one APW/SW to the biological tissue specimen.

15. An apparatus according to claim 14, wherein said tissue-specimen receiving region is designed and configured to receive a biological tissue specimen undergoing histology processing for microscopic examination, and said control system is designed and configured to control said APW/SW system in a manner that provides an improvement to a histotechnological processing step.

16. A system, comprising:
    a tissue-specimen receiving region containing a biological tissue specimen undergoing processing to create a processed specimen for examination;
    an acoustic pressure wave/shock wave (APW/SW) system that includes at least one APW/SW generator designed, configured, and located relative to said tissue-specimen receiving region, so as to apply at least one APW/SW to said biological tissue specimen; and
    a control system designed and configured to control said APW/SW system in a predetermined manner that provides an improvement to said processed specimen that would not exist without the application of the at least one APW/SW to said biological tissue specimen.

* * * * *